(12) United States Patent
Fukushima et al.

(10) Patent No.: US 11,002,708 B2
(45) Date of Patent: May 11, 2021

(54) PHOTOACOUSTIC MICROSCOPE OBJECTIVE LENS UNIT AND PHOTOACOUSTIC MICROSCOPE INCLUDING THE SAME

(71) Applicant: OLYMPUS CORPORATION, Tokyo (JP)

(72) Inventors: Ikutoshi Fukushima, Fuchu (JP); Asuka Mukai, Higashiyamato (JP); Yoshiaki Murayama, Machida (JP)

(73) Assignee: OLYMPUS CORPORATION, Tokyo (JP)

(*) Notice: Subject to any disclaimer, the term of this patent is extended or adjusted under 35 U.S.C. 154(b) by 987 days.

(21) Appl. No.: 15/637,605

(22) Filed: Jun. 29, 2017

(65) Prior Publication Data

US 2017/0299553 A1    Oct. 19, 2017

Related U.S. Application Data

(63) Continuation of application No. PCT/JP2015/050294, filed on Jan. 7, 2015.

(51) Int. Cl.
*G01N 29/06* (2006.01)
*G02B 21/02* (2006.01)
(Continued)

(52) U.S. Cl.
CPC ....... *G01N 29/0663* (2013.01); *A61B 5/0095* (2013.01); *A61B 8/13* (2013.01);
(Continued)

(58) Field of Classification Search
CPC .............. G01N 29/0663; G01N 29/06; G01N 29/0672; G01N 29/22; G01N 29/24;
(Continued)

(56) References Cited

U.S. PATENT DOCUMENTS 4,745,270 A * 5/1988 Horikawa ............ G02B 21/002
                                                       250/216
4,800,269 A * 1/1989 Horikawa ............ G02B 21/002
                                                       250/234
(Continued)

FOREIGN PATENT DOCUMENTS

CN       207532377 U  *  6/2018    ........... A61B 5/0095
JP       H04-292153 A     10/1992
(Continued)

OTHER PUBLICATIONS

Translation CN-207532377-U (Year: 2018).*
(Continued)

*Primary Examiner* — Alexander A Mercado
*Assistant Examiner* — Monica S Young
(74) *Attorney, Agent, or Firm* — Scully, Scott, Murphy & Presser, P.C.

(57) ABSTRACT

A photoacoustic microscope objective lens unit includes: an objective lens which irradiates a sample with excitation light L; a photoacoustic wave detection unit which detects a photoacoustic wave U generated from the sample; and a photoacoustic wave guide system. The photoacoustic wave guide system includes: a photoacoustic wave separation member; and an acoustic lens that is disposed between the photoacoustic wave separation member and the sample and has a focus position that substantially matches with a focus position of the objective lens. The acoustic lens is obtained by cementing a main acoustic lens and a correction acoustic lens to each other. The main acoustic lens and the correction acoustic lens satisfy predetermined Conditional Expressions.

10 Claims, 7 Drawing Sheets

(51) Int. Cl.
*G02B 21/00* (2006.01)
*G01N 29/22* (2006.01)
*G01N 29/24* (2006.01)
*A61B 5/00* (2006.01)
*A61B 8/13* (2006.01)
*G10K 11/30* (2006.01)

(52) U.S. Cl.
CPC ......... *G01N 29/06* (2013.01); *G01N 29/0672* (2013.01); *G01N 29/22* (2013.01); *G01N 29/24* (2013.01); *G01N 29/2418* (2013.01); *G02B 21/002* (2013.01); *G02B 21/0028* (2013.01); *G02B 21/02* (2013.01); *A61B 5/0073* (2013.01)

(58) Field of Classification Search
CPC .... G01N 29/2418; A61B 5/0095; A61B 8/13; A61B 5/0073; G02B 21/002; G02B 21/0028; G02B 21/02; G10K 11/30
USPC ........................................................ 73/643
See application file for complete search history.

(56) References Cited

U.S. PATENT DOCUMENTS

| | | | | |
|---|---|---|---|---|
| 4,880,012 | A * | 11/1989 | Sato | A61B 8/4281 600/472 |
| 5,127,410 | A | 7/1992 | King et al. | |
| 5,161,053 | A * | 11/1992 | Dabbs | G02B 21/0032 359/384 |
| 8,454,512 | B2 | 6/2013 | Wang et al. | |
| 8,997,572 | B2 * | 4/2015 | Wang | G02B 26/105 73/606 |
| 2008/0281237 | A1 * | 11/2008 | Slayton | A61B 8/4281 601/2 |
| 2010/0268042 | A1 * | 10/2010 | Wang | G01N 29/2418 600/322 |
| 2013/0301114 | A1 | 11/2013 | Sangawa et al. | |
| 2016/0038770 | A1 * | 2/2016 | Tyler | A61N 7/02 601/2 |
| 2016/0183782 | A1 * | 6/2016 | Yu | A61B 3/18 351/206 |

FOREIGN PATENT DOCUMENTS

| | | |
|---|---|---|
| JP | H11-285496 A | 10/1999 |
| JP | 2011-519281 A | 7/2011 |
| JP | 5308597 B1 | 10/2013 |

OTHER PUBLICATIONS

Aden, M., Roesner, A. and Olowinsky, A. (2010), Optical characterization of polycarbonate: Influence of additives on optical properties. J. Polym. Sci. B Polym. Phys., 48: 451-455. https://doi.org/10.1002/polb.21906 (Year: 2010).*

Table of Ultrasonic Properties https://www.bostonpiezooptics.com/ultrasonic-properties Boston Piezo Optics (Year: 2020).*

Transmission spectrum for polycarbonate https://en.wikipedia.org/wiki/Polycarbonate#/media/File:VisibleLightSpectrum2.svg (Year: 2015).*

Plastics Ultrasonic Properties https://www.ndt.net/links/proper.htm (Year: 1985).*

International Search Report dated Apr. 7, 2015 issued in PCT/JP2015/050294.

English translation of International Preliminary Report on Patentability dated Jul. 20, 2017 together with the Written Opinion received in related International Application No. PCT/JP2015/050294.

* cited by examiner

PHOTOACOUSTIC MICROSCOPE OBJECTIVE LENS UNIT AND PHOTOACOUSTIC MICROSCOPE INCLUDING THE SAME

CROSS-REFERENCE TO RELATED APPLICATION

The present application is a continuation application of PCT/JP2015/050294 filed on Jan. 7, 2015 which is based upon and claims the benefit of priority from PCT/JP2015/050294; the entire contents of which are incorporated herein by reference.

BACKGROUND OF THE INVENTION

Field of the Invention

The present invention relates to a photoacoustic microscope objective lens unit and a photoacoustic microscope including the same.

Description of the Related Art

Photoacoustic waves are one kind of elastic waves generated in the process of thermoelastic phenomenon caused when a substance is irradiated with light having an absorption wavelength band. Photoacoustic imaging is thus drawing attention as a method for imaging absorption characteristics. Elastic waves, which are one kind of ultrasonic waves, have characteristics of being less affected by scattering than light, and are thus applied as imaging means for the inside of a living body.

A photoacoustic microscope, which applies photoacoustic waves to a detection signal for imaging, employs a method involving using pulse light adjusted to an absorption wavelength band of an object to be observed as excitation light, scanning a sample with a spot focused by a focusing objective lens, and detecting photoacoustic waves generated at each spot by a transducer or other such devices. When the sample is scanned with the spot, photoacoustic waves are generated if an absorbing substance is present at the focus position. Detecting the photoacoustic waves, absorption characteristics in the sample can be imaged with the use of the photoacoustic microscope.

Figure 6:
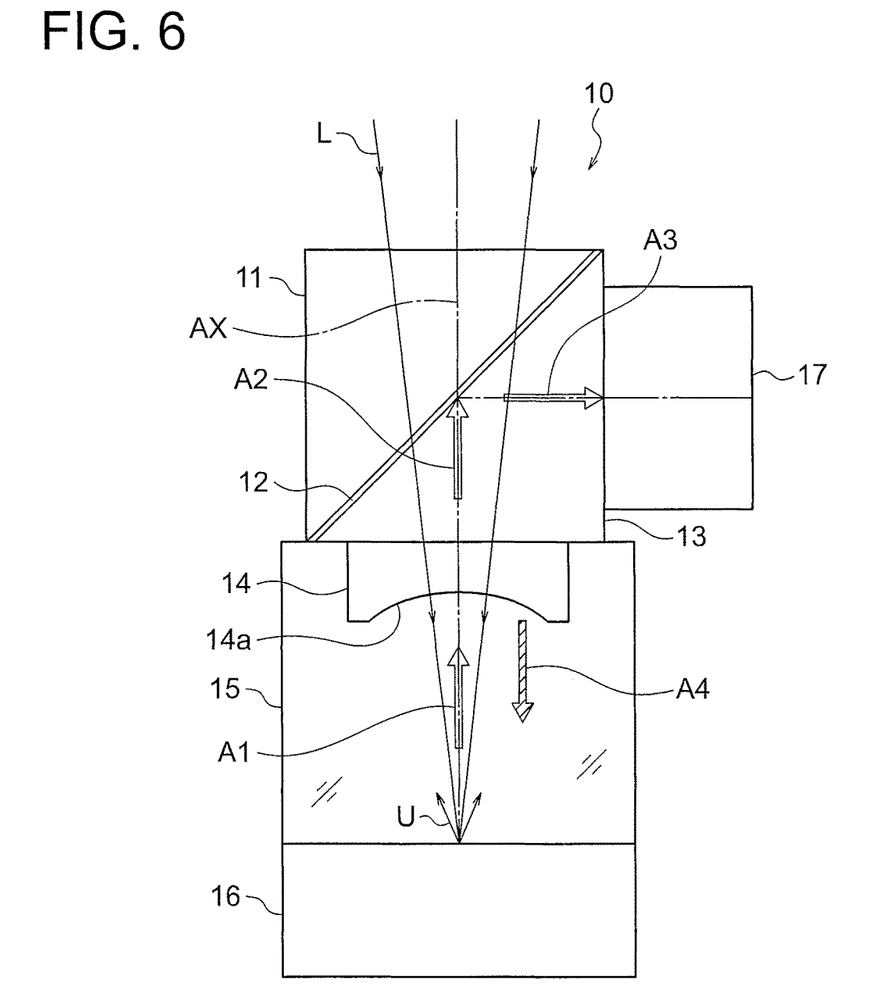
FIG. 6 is a diagram illustrating a configuration of a conventional photoacoustic microscope apparatus.
Figure 7:
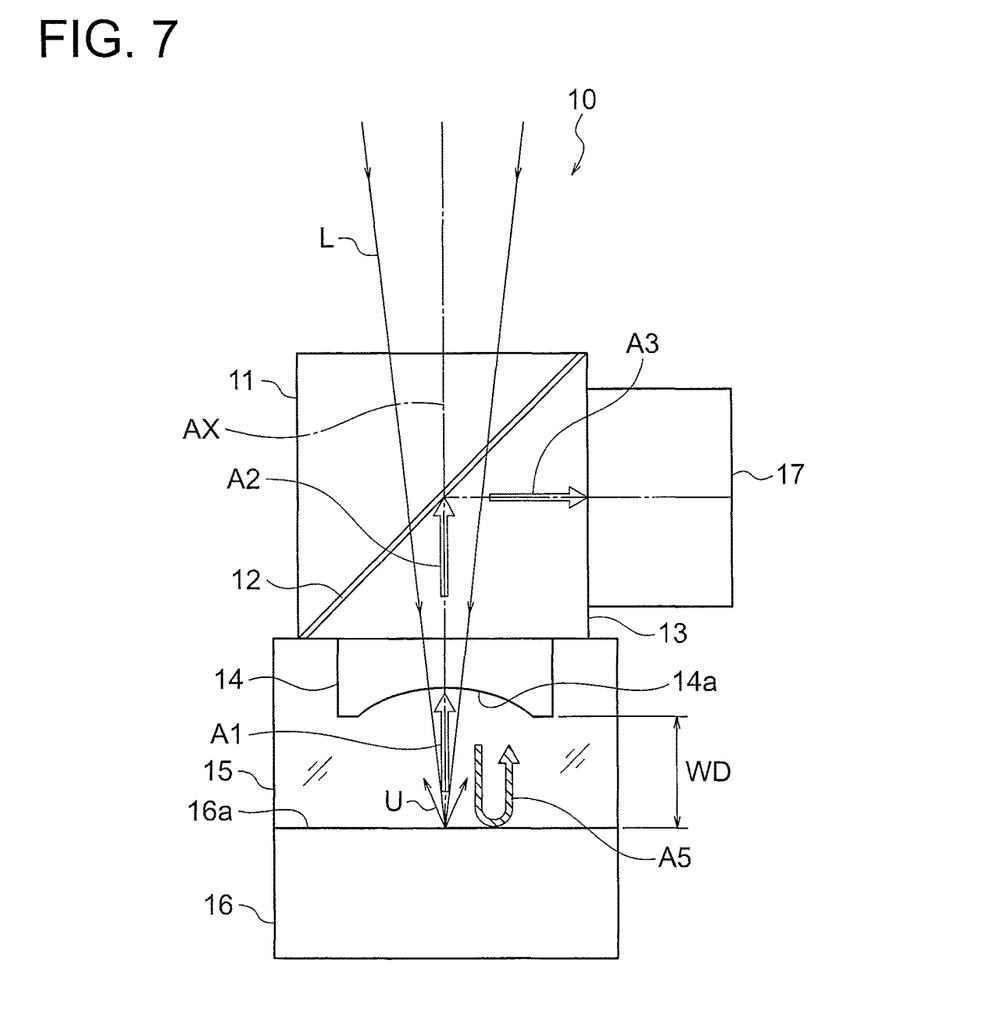
FIG. 7 is another diagram illustrating the configuration of the conventional photoacoustic microscope apparatus.

Such a photoacoustic microscope is proposed in, for example, Japanese Patent Application Publication No. 2011-519281 and Japanese Patent No. 5308597. FIG. 6 and FIG. 7 schematically illustrate the configuration of a conventional photoacoustic microscope. Excitation light L from a laser pulse light source (not shown) passes through a condenser lens (not shown), a triangular prism 11, silicone oil 12, a triangular prism 13, and an ultrasonic lens 14 to be focused on a sample 16. The triangular prisms 11 and 13 are coupled through the silicone oil 12. Photoacoustic waves U generated from the sample travel in the directions of the arrows A1 and A2, pass through the triangular prism 13, and are reflected by the silicone oil 12. The photoacoustic waves U reflected by the silicone oil 12 travel in the direction of the arrow A3 to be detected by the ultrasound transducer 17. The space between the ultrasonic lens 14 and the sample 16 is filled with a photoacoustic wave transmission medium 15.

SUMMARY OF THE INVENTION

A photoacoustic microscope objective lens unit of the present invention includes: an objective lens which irradiates a sample with excitation light having an absorption wavelength band of an object to be observed; a photoacoustic wave detection unit which detects a photoacoustic wave generated from the sample through irradiation of the excitation light; and a photoacoustic wave guide system which guides the photoacoustic wave to the photoacoustic wave detection unit, in which the photoacoustic wave guide system includes: a photoacoustic wave separation member which transmits the excitation light traveling from the objective lens and reflects a photoacoustic wave generated from the sample; and an acoustic lens that is disposed between the photoacoustic wave separation member and the sample and having a focus position that substantially matches with a focus position of the objective lens, the acoustic lens is formed by cementing a main acoustic lens disposed on the photoacoustic wave separation member side and a correction acoustic lens disposed on the sample side to suppress reflection of the photoacoustic wave, and the main acoustic lens and the correction acoustic lens satisfy the following Conditional Expressions (1) and (2):

$$0.8 < T0 \leq 1.0 \quad (1)$$

$$Z2 < Z0 < Z1 \quad (2)$$

where $T0$ is a transmittance of the correction acoustic lens with respect to the excitation light on an optical axis, $Z0$ is acoustic impedance of a medium of the correction acoustic lens, $Z1$ is acoustic impedance of a medium of the main acoustic lens, and $Z2$ is acoustic impedance of a medium that is brought into contact with the correction acoustic lens on the sample side during detection of the photoacoustic wave.

A photoacoustic microscope of the present invention includes: the above-mentioned photoacoustic microscope objective lens unit; and a scanning unit which scan a sample with excitation light while moving an irradiation position of the excitation light.

DETAILED DESCRIPTION OF THE INVENTION

Functions and effects obtained by the configuration of a photoacoustic microscope objective lens unit and a photoacoustic microscope in embodiments are now described. The present invention is not intended to be limited by the embodiments. Specifically, the description of embodiments includes many specific detailed contents for the illustrative purposes, but various variations and changes of the detailed contents do not depart from the scope of the present invention. Thus, the illustrative embodiments of the present invention are described below without loss of generality or any limitation on the claimed invention.

First Embodiment

Figure 1:
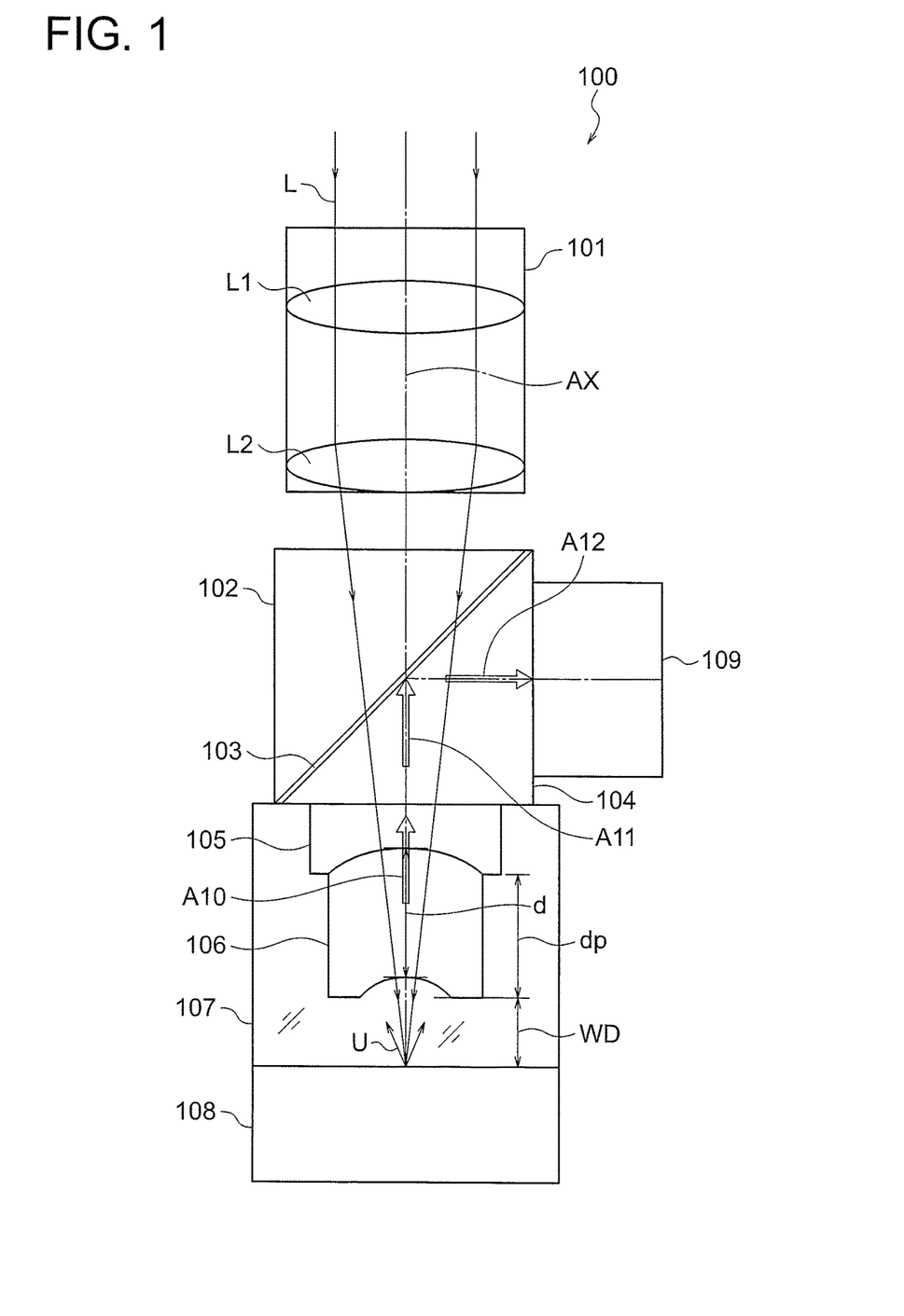
FIG. 1 is a diagram illustrating a configuration of a photoacoustic microscope objective lens unit according to a first embodiment of the present invention.

FIG. 1 illustrates a configuration of a photoacoustic microscope objective lens unit 100 according to a first embodiment. The photoacoustic microscope objective lens unit in the first embodiment is suitable for epi-illumination.

The photoacoustic microscope objective lens unit 100 includes an objective lens 101, a triangular prism 102, a photoacoustic wave reflective member 103, a triangular prism 104, a main acoustic lens 105, a correction acoustic lens 106, and an ultrasound transducer 109.

The objective lens 101 is formed of, for example, lenses L1 and L2. The objective lens 101 illustrates a sample 108 with excitation light L having an absorption wavelength band of an object to be observed.

The triangular prisms 102 and 104 are disposed between the objective lens 101 and the sample 108. In FIG. 1, the triangular prisms 102 and 104 are right triangular prisms, and inclined surfaces thereof are bonded through the photoacoustic wave reflective member 103.

The photoacoustic wave reflective member 103 is a member that is transparent for the excitation light L and has an acoustic impedance different from those of the triangular prisms 102 and 104, such as silicone oil.

The main acoustic lens 105 is disposed so as to be coaxial with an optical axis AX of the objective lens 101 in a manner that the main acoustic lens 105 is cemented to a surface of the triangular prism 104 from which the excitation light L is output. Focus positions of the main acoustic lens 105 and the correction acoustic lens 106 substantially match with a focus position of the objective lens 101.

The ultrasound transducer 109 forms a photoacoustic wave detection unit, and is disposed to detect photoacoustic waves U that pass through the correction acoustic lens 106 and the main acoustic lens 105 to enter the ultrasound transducer 109. The main acoustic lens 105 and the correction acoustic lens 106 form an acoustic lens. The correction acoustic lens 106 suppresses the reflection of the photoacoustic waves U as described later.

In the above-mentioned configuration, excitation light (pulse light) L from a laser pulse light source (not shown) passes through the objective lens 101, the triangular prism 102, the photoacoustic wave reflective member 103, the triangular prism 104, the main acoustic lens 105, and the correction acoustic lens 106 to irradiate the sample 108. The applied excitation light L is focused on the surface or in the inside of the sample 108.

A photoacoustic wave transmission medium 107 through which photoacoustic waves U easily propagate, such as water, is filled between the triangular prism 104 and the sample 108.

For example, when the sample 108 is a living body and blood vessels in the living body are intended to be imaged, excitation light L having an absorption wavelength of hemoglobin is used. The object to be observed is not limited to blood vessels, and the present invention is applicable to imaging of endogenous substances, such as melanin. In this case, light having an absorption wavelength band of a substance to be observed is used as excitation light. The present invention is also applicable to imaging of exogenous substances, such as phosphor and metal nanoparticles.

For phosphor, light having an absorption wavelength band of phosphor to be observed is used as excitation light. For metal nanoparticles, light having a resonance wavelength band of metal nanoparticles to be observed is used as excitation light. When a plurality of absorbing substances are present in the sample 108, it is desired to use light having a peak wavelength of an absorption spectrum characteristic to an object to be observed.

When an object to be observed that absorbs the excitation light L is present at an irradiation region of the excitation light L including the focus position of the objective lens 101, the excitation light L applied to the sample 108 is absorbed by the object to be observed. In response thereto, photoacoustic waves U as elastic waves are generated from the sample 108. The generated photoacoustic waves U pass through the correction acoustic lens 106, the main acoustic lens 105, and the triangular prism 104 to be detected by the ultrasound transducer 109. At least the triangular prism 102, the photoacoustic wave reflective member 103, and the triangular prism 104 form a photoacoustic wave separation member. The photoacoustic wave separation member transmits the excitation light L traveling from the objective lens 101 and reflects the photoacoustic waves U generated from the sample 108.

The triangular prism 102, the photoacoustic wave reflective member 103, the triangular prism 104, the main acoustic lens 105, and the correction acoustic lens 106 form a photoacoustic wave guide system.

The photoacoustic waves U generated from the sample 108 are focused by the correction acoustic lens 106 and the main acoustic lens 105 to enter the triangular prism 104 as plane waves. The plane waves are reflected by an inclined plane of the triangular prism 104 with acoustic impedance of the photoacoustic wave reflective member 103. The photoacoustic wave reflective member 103 is preferably designed such that the refractive index for the excitation light L substantially matches with refractive indices of the triangular prisms 102 and 104 and the thickness is as small as possible. This configuration can prevent unnecessary refraction and light absorption by the photoacoustic wave reflective member 103, thereby improving use efficiency of the excitation light L.

The photoacoustic waves U reflected by the inclined plane of the triangular prism 104 in the direction of the arrow A12 are output from the triangular prism 104. The output photoacoustic waves U are detected by the ultrasound transducer 109. The ultrasound transducer 109 forms a photoacoustic wave detection unit.

In the photoacoustic microscope objective lens unit 100 according to the first embodiment, as described above, the acoustic lens is formed by cementing the main acoustic lens 105 disposed on the photoacoustic wave reflective member 103 side and the correction acoustic lens 106 disposed on the sample 108 side to suppress the reflection of the photoacoustic waves U.

The main acoustic lens 105 is disposed between the photoacoustic wave separation member 103 and the sample 108, and has a focus position that substantially matches with a focus position of the objective lens 101. For example, the main acoustic lens 105 converts the wavefront of the photoacoustic wave U into a flat wavefront.

It is desired that the main acoustic lens 105 and the correction acoustic lens 106 satisfy the following Conditional Expressions (1) and (2):

$$0.8 < T0 \leq 1.0 \quad (1)$$

$$Z2 < Z0 < Z1 \quad (2)$$

where

T0 is a transmittance of the correction acoustic lens 106 with respect to the excitation light on the optical axis AX, Z0 is acoustic impedance (kg/(m²s)) of the medium of the correction acoustic lens 106, Z1 is acoustic impedance (kg/(m²s)) of the medium of the main acoustic lens 105, and Z2 is acoustic impedance (kg/(m²s)) of a medium that is brought into contact with the correction acoustic lens 106 on the sample 108 side during detection of the photoacoustic wave U.

The correction acoustic lens 106, which is designed such that T0 does not fall below the lower limit value in Conditional Expression (1), can irradiate the sample 108 with the excitation light L while maintaining the intensity of the excitation light L. In this manner, high optical signal intensity can be obtained.

T0 does not exceed the upper limit value in Conditional Expression (1).

Disposing the correction acoustic lens 106 satisfying Conditional Expression (2) between the medium on the sample 108 side and the main acoustic lens 105 enables the reflection of the photoacoustic wave U by the acoustic lens to be suppressed.

Preferably, when both the conditions in Conditional Expressions (1) and (2) are satisfied, an acoustic lens including a more preferable correction acoustic lens 106 can be formed.

It is more preferred to set the lower limit value in Conditional Expression (1) to be 0.85.

When the upper limit value in Conditional Expression (1) is set to be 0.98 and T0 is set not to fall below the upper limit value, the thickness of the correction acoustic lens 106 can be appropriately secured by an available material, which is more preferable.

The lower limit value in Conditional Expression (2) is set to be preferably 1.4×Z2, more preferably 2×Z2. The upper limit value in Conditional Expression (2) is set to be preferably 0.7×Z1, more preferably 0.5×Z1.

In the first embodiment, it is desired to satisfy the following Conditional Expression (2-1):

$$1.5 \times 10^6 (kg/(m^2s)) < Z0 < Z1 \quad (2\text{-}1)$$

where

Z0 is acoustic impedance (kg/(m²s)) of the medium of the correction acoustic lens 106, and Z1 is acoustic impedance (kg/(m²s)) of the medium of the main acoustic lens 105.

In particular, when the sample is a biological sample, the medium on the sample 108 side is generally water. Alcohol may be used as the medium on the sample 108 side. It is therefore preferred to set the lower limit value in Conditional Expression (2-1) to be 1.5×10⁶ (kg/(m²s)), which is the acoustic impedance value of water.

It is desired that the medium of the main acoustic lens 105 be glass. Glass has high transmittance for the excitation light L and is effective for the correction of the photoacoustic wave (ultrasonic waves) U, and is thus suited for the main acoustic lens 105. Glass has high acoustic impedance, but the use of the above-mentioned correction acoustic lens 106 can reduce the reflection of photoacoustic waves U traveling from the sample 108 at the interface.

It is desired that the correction acoustic lens 106 satisfy the following Conditional Expression (3):

$$s \times d < (Z2 - Z1)^2 / (Z2 + Z1)^2 \quad (3)$$

where s is a scattering coefficient of the medium of the correction acoustic lens 106 with respect to excitation light L, d is the thickness of the correction acoustic lens 106 on the optical axis AX, Z1 is acoustic impedance (kg/(m²s)) of the medium of the main acoustic lens 105, and Z2 is acoustic impedance (kg/(m²s)) of a medium that is brought into contact with the correction acoustic lens 106 on the sample 108 side during detection of the photoacoustic wave U.

Satisfying Conditional Expression (3) can suppress the thickness d and the scattering coefficient s of the correction acoustic lens 106. In this manner, the loss of the photoacoustic wave U can be reduced as compared with the case where the correction acoustic lens 106 is not used. The loss of the excitation light L can be reduced to maintain the intensity of the excitation light L. This configuration is also effective for maintaining a working distance WD.

It is more preferred to set the upper limit value in Conditional Expression (3) to be $0.5 \times (Z2-Z1)^2/(Z2+Z1)^2$.

It is desired that the correction acoustic lens 106 satisfy the following Conditional Expression (4):

$$\alpha \times d < (Z2 - Z1)^2 / (Z2 + Z1)^2 \quad (4)$$

where

α is an absorption coefficient of a medium of the correction acoustic lens 106 with respect to the excitation light L, d is the thickness of the correction acoustic lens 106 on the optical axis AX, Z1 is acoustic impedance (kg/(m²s)) of the medium of the main acoustic lens 105, and Z2 is acoustic impedance (kg/(m²s)) of a medium that is brought into contact with the correction acoustic lens 106 on the sample 108 side during detection of the photoacoustic wave U.

Satisfying Conditional Expression (4) can suppress the thickness d and the scattering coefficient α of the correction acoustic lens 106. In this manner, the intensity of the excitation light L can be maintained. This configuration is advantageous for maintaining a working distance WD.

It is more preferred to set the upper limit value in Conditional Expression (4) to be $0.5 \times (Z2-Z1)^2/(Z2+Z1)^2$.

It is desired that the correction acoustic lens 106 satisfy the following Conditional Expression (5):

$$1.0 < d/\lambda \quad (5)$$

where d is the thickness of the correction acoustic lens 106 on the optical axis AX, and λ is the wavelength of the photoacoustic wave (ultrasonic wave) U in the air.

Satisfying Conditional Expression (5) can provide an appropriate thickness to the correction acoustic lens 106. Accordingly, the correction acoustic lens 106 can have the function of a lens and the role of a buffer member. Glass is hard, and hence if the correction acoustic lens 106 is made of glass, when the sample 108 is a living body, the correction acoustic lens 106 and the sample 108 may contact with each other to damage the sample 108. The role of a buffer member, which is obtained by the effect in the first embodiment, means that when the correction acoustic lens 106 is made of a material softer than glass, even if a working distance WD is short and a distal end portion of the correction acoustic lens 106 and the sample 108 contact with each other, the damage of the sample 108 can be reduced as described later.

It is more preferred to set the lower limit value in Conditional Expression (5) to be 1.5.

It is desired that a difference between the thickness d of the correction acoustic lens 106 on the optical axis AX and the thickness dp of the correction acoustic lens 106 at a peripheral portion be larger than a half of the wavelength $\lambda$ of the photoacoustic wave U in the air. This configuration can provide the correction acoustic lens 106 with an optical lens function, which is more preferable.

It is desired that a surface of the correction acoustic lens 106 on the sample 108 side be a concave surface or a flat surface. This configuration can secure the working distance WD, which is preferable. In particular, when the surface of the correction acoustic lens 106 on the sample 108 side is a flat surface, the processing of the correction lens is facilitated, which is more preferable.

It is desired that the correction acoustic lens 106 satisfy at least one of the following Conditional Expression (6-1) or Conditional Expression (6-2):

$$|n0-n2|<0.1 \quad (6\text{-}1)$$

$$|n0-n1|<0.1 \quad (6\text{-}2)$$

where n0 is a refractive index of the medium of the correction acoustic lens 106 with respect to excitation light L, n1 is a refractive index of the medium of the main acoustic lens 105 with respect to excitation light L, and n2 is a refractive index of a medium that is brought into contact with the correction acoustic lens 106 on the sample 108 side with respect to the excitation light L during detection of the photoacoustic wave U (ultrasonic wave).

When any one of Conditional Expression (6-1) and Conditional Expression (6-2) is satisfied, the difference in refractive index between the correction acoustic lens 106 and an adjacent medium can be reduced. In this manner, the correction acoustic lens 106 can be easily designed.

It is more preferred to set each of the upper limit values in Conditional Expression (6-1) and Conditional Expression (6-2) to be 0.05.

It is desired that the correction acoustic lens 106 be formed of a material obtained by solidifying water with a coagulant into a gel. This configuration can easily obtain the above-mentioned characteristics suited for the correction acoustic lens 106. In the first embodiment, the correction acoustic lens 106 is formed of a member obtained by solidifying water with polyvinyl alcohol (PVA).

For stabilizing the shape, the periphery of the correction acoustic lens 106 may be reinforced.

As a reinforcing member, metal or plastic may be used to surround the periphery of a region through which light beams pass and the periphery of a lens. It is more preferred to use an opaque member as the reinforcing member.

Second Embodiment

Figure 2:
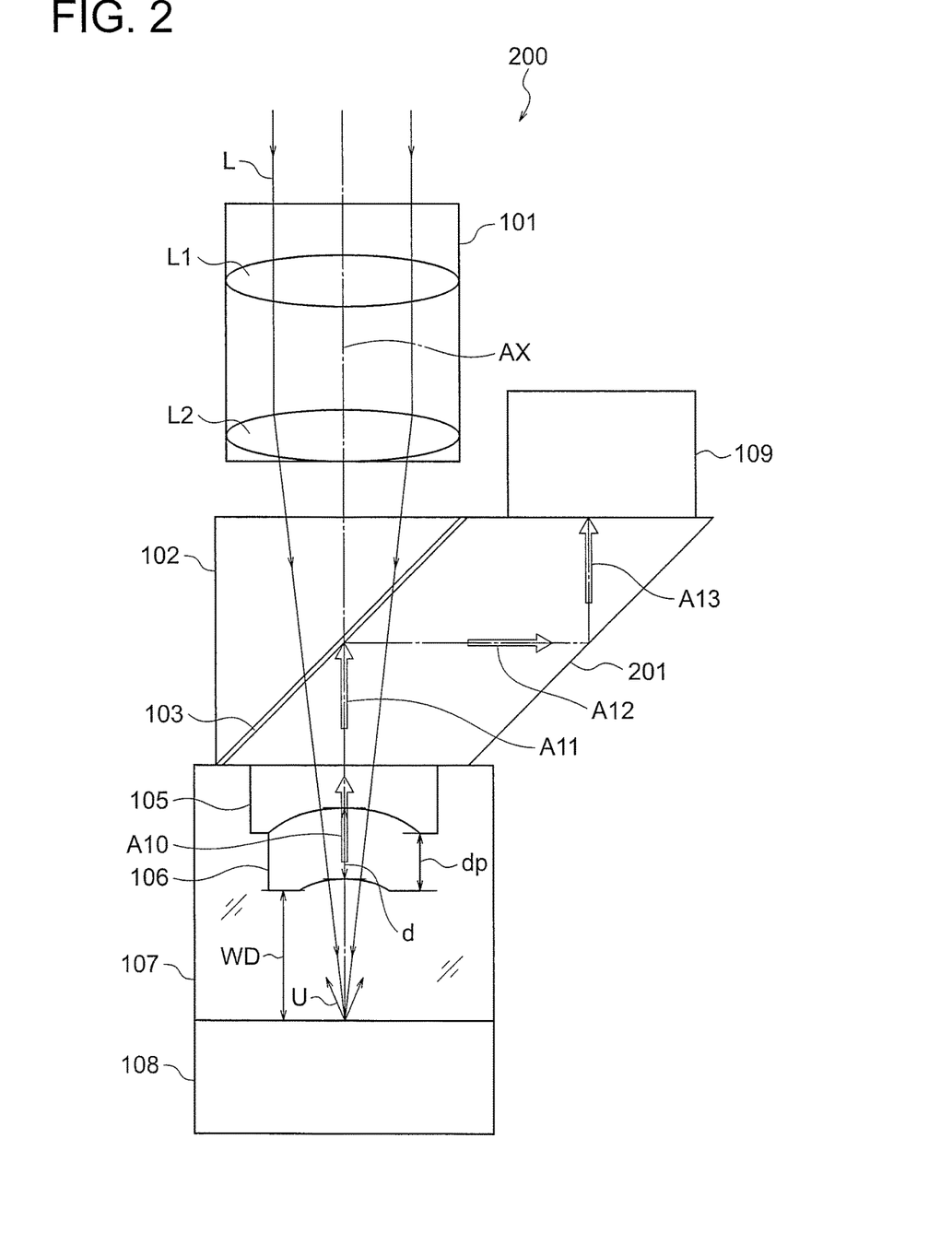
FIG. 2 is a diagram illustrating a configuration of a photoacoustic microscope objective lens unit according to a second embodiment of the present invention.

FIG. 2 illustrates a schematic configuration of a photoacoustic microscope objective lens unit 200 according to a second embodiment of the present invention. The same parts as in the first embodiment are denoted by the same reference symbols to omit overlapping descriptions. The photoacoustic microscope objective lens unit in the second embodiment is suitable for epi-illumination.

Excitation light (pulse light) L from a laser pulse light source (not shown) passes through the objective lens 101, the triangular prism 102, the photoacoustic wave reflective member 103, the rhomboid prism (rhomboidal prism) 201, the main acoustic lens 105, and the correction acoustic lens 106 to irradiate the sample 108. The applied excitation light L is focused on the surface or in the inside of the sample 108.

A photoacoustic wave transmission medium 107 through which photoacoustic waves U easily propagate, such as water, is filled between the rhomboid prism 201 and the sample 108.

When an object to be observed that absorbs the excitation light L is present at an irradiation region of the excitation light L including the focus position of the objective lens 101, the excitation light L applied to the sample 108 is absorbed by the object to be observed. In response thereto, photoacoustic waves U as elastic waves are generated from the sample 108. The generated photoacoustic waves U pass through the correction acoustic lens 106, the main acoustic lens 105, and the rhomboid prism 201 to be detected by the ultrasound transducer 109. The triangular prism 102, the photoacoustic wave reflective member 103, and the rhomboid prism 201 form a photoacoustic wave separation member. The photoacoustic wave separation member transmits the excitation light L traveling from the objective lens 101 and reflects the photoacoustic waves U generated from the sample 108.

Photoacoustic waves U generated from the sample 108 are focused by the correction acoustic lens 106 and the main acoustic lens 105 to enter the rhomboid prism 201 as plane waves. The plane waves are reflected by an inclined plane of the rhomboid prism 201 with acoustic impedance of the photoacoustic wave reflective member 103. The photoacoustic wave reflective member 103 is preferably designed such that the refractive index for the excitation light L substantially matches with refractive indices of the triangular prism 102 and the rhomboid prism 201 and the thickness is as small as possible. This configuration can prevent unnecessary refraction and light absorption by the photoacoustic wave reflective member 103, thereby improving use efficiency of the excitation light L.

The photoacoustic waves U reflected by the inclined plane of the rhomboid prism 201 in the direction of the arrow A12 are reflected again by another inclined plane in the direction of the arrow A13 and output from the rhomboid prism 201. The output photoacoustic waves U are detected by the ultrasound transducer 109. The ultrasound transducer 109 forms a photoacoustic wave detection unit. In the second embodiment, the triangular prism 102, the photoacoustic wave reflective member 103, and the rhomboid prism 201 form a photoacoustic wave separation member. The photoacoustic wave separation member guides the photoacoustic waves U to the photoacoustic wave detection unit.

The triangular prism 102, the photoacoustic wave reflective member 103, the rhomboid prism 201, the main acoustic lens 105, and the correction acoustic lens 106 form a photoacoustic wave guide system.

As described above, in the photoacoustic microscope objective lens unit 200 according to the second embodiment, the acoustic lens is formed by cementing the main acoustic lens 105 disposed on the photoacoustic wave reflective member 103 side and the correction acoustic lens 106 disposed on the sample 108 side to suppress the reflection of the photoacoustic waves U.

The acoustic lens is disposed between the photoacoustic wave separation member 103 and the sample 108, and has a focus position that substantially matches with the focus position of the objective lens 101. For example, the acoustic lens converts the wavefront of the photoacoustic wave U into a flat wavefront.

It is desired that the main acoustic lens 105 and the correction acoustic lens 106 satisfy the above-mentioned Conditional Expressions (1) and (2).

In the second embodiment, it is desired to satisfy the above-mentioned Conditional Expression (2-1).

In particular, when the sample 108 is a biological sample, the medium on the sample 108 side is generally water. Alcohol may be used as the medium on the sample 108 side. It is therefore preferred to set the lower limit value in Conditional Expression (2-1) to be $1.5 \times 10^6$ (kg/(m²s)), which is the acoustic impedance value of water.

It is desired that the medium of the main acoustic lens 105 be glass. Glass has high transmittance to the excitation light L and is advantageous for the correction of the photoacoustic waves (ultrasonic waves) U, and is therefore suited for the main acoustic lens 105. Glass has high acoustic impedance, but the use of the above-mentioned correction acoustic lens 106 can reduce the reflection of ultrasonic waves (photoacoustic waves) traveling from the sample 108 at the interface.

It is desired that the correction acoustic lens 106 satisfy the above-mentioned Conditional Expression (3).

It is desired that the correction acoustic lens 106 satisfy the above-mentioned Conditional Expression (4).

It is desired that the correction acoustic lens 106 satisfy the above-mentioned Conditional Expression (5).

It is desired that the difference between the thickness d of the correction acoustic lens 106 on the optical axis AX and the thickness dp of the correction acoustic lens 106 at a peripheral portion be larger than a half of the wavelength λ of the photoacoustic wave U in the air.

It is desired that a surface of the correction acoustic lens 106 on the sample 108 side be a concave surface or a flat surface.

It is desired that the correction acoustic lens 106 satisfy at least one of the above-mentioned Conditional Expression (6-1) or Conditional Expression (6-2).

In the second embodiment, the correction acoustic lens 106 is formed from an epoxy resin.

Third Embodiment

Figure 3:
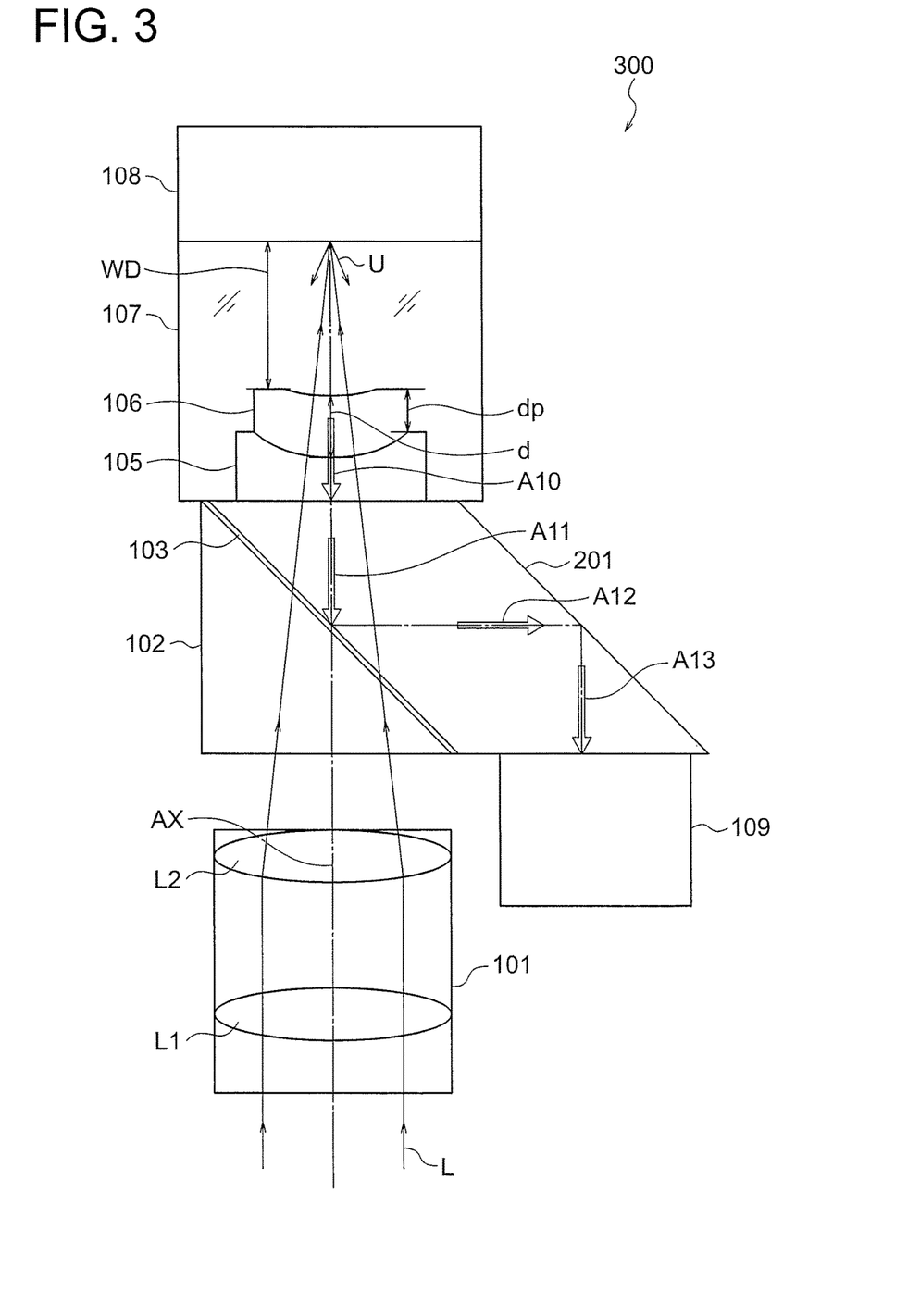
FIG. 3 is a diagram illustrating a configuration of a photoacoustic microscope objective lens unit according to a third embodiment of the present invention.

FIG. 3 illustrates a schematic configuration of a photoacoustic microscope objective lens unit 300 according to a third embodiment of the present invention. The same parts as in the first embodiment are denoted by the same reference symbols to omit overlapping descriptions. The photoacoustic microscope objective lens unit in the third embodiment is suited for inverted illumination.

Excitation light (pulse light) L from a laser pulse light source (not shown) passes through the objective lens 101, the triangular prism 102, the photoacoustic wave reflective member 103, the rhomboid prism (rhomboidal prism) 201, the main acoustic lens 105, and the correction acoustic lens 106 to irradiate the sample 108. The applied excitation light L is focused on the surface or in the inside of the sample 108.

A photoacoustic wave transmission medium 107 through which photoacoustic waves U easily propagate, such as water, is filled between the rhomboid prism 201 and the sample 108.

When an object to be observed that absorbs the excitation light L is present at an irradiation region of the excitation light L including the focus position of the objective lens 101, the excitation light L applied to the sample 108 is absorbed by the object to be observed. In response thereto, photoacoustic waves U as elastic waves are generated from the sample 108. The generated photoacoustic waves U pass through the correction acoustic lens 106, the main acoustic lens 105, and the rhomboid prism 201 to be detected by the ultrasound transducer 109. At least the triangular prism 102, the photoacoustic wave reflective member 103, and the rhomboid prism 201 form a photoacoustic wave separation member. The photoacoustic wave separation member transmits the excitation light L traveling from the objective lens 101 and reflects the photoacoustic waves U generated from the sample 108.

The triangular prism 102, the photoacoustic wave reflective member 103, the rhomboid prism 201, the main acoustic lens 105, and the correction acoustic lens 106 form a photoacoustic wave guide system.

Photoacoustic waves U generated from the sample 108 are focused by the correction acoustic lens 106 and the main acoustic lens 105 to enter the rhomboid prism 201 as plane waves. The plane waves are reflected by an inclined plane of the rhomboid prism 201 with acoustic impedance of the photoacoustic wave reflective member 103. The photoacoustic wave reflective member 103 is preferably designed such that the refractive index for the excitation light L substantially matches with refractive indices of the triangular prism 102 and the rhomboid prism 201 and the thickness is as small as possible. This configuration can prevent unnecessary refraction and light absorption by the photoacoustic wave reflective member 103, thereby improving use efficiency of the excitation light L.

The photoacoustic waves U reflected by the inclined plane of the rhomboid prism 201 in the direction of the arrow A12 are reflected by another inclined plane of the rhomboid prism 201 in the direction of the arrow A13 and output from the rhomboid prism 201. The output photoacoustic waves U are detected by the ultrasound transducer 109. The ultrasound transducer 109 forms a photoacoustic wave detection unit.

As described above, in the photoacoustic microscope objective lens unit 100 according to the third embodiment, the acoustic lens is formed by cementing the main acoustic lens 105 disposed on the photoacoustic wave reflective member 103 side and the correction acoustic lens 106 disposed on the sample 108 side to suppress the reflection of the photoacoustic waves U.

The acoustic lens is disposed between the photoacoustic wave separation member and the sample 108, and has a focus position that substantially matches with the focus position of the objective lens 101. For example, the acoustic lens converts the wavefront of the photoacoustic wave U into a flat wavefront.

It is desired that the main acoustic lens 105 and the correction acoustic lens 106 satisfy the above-mentioned Conditional Expressions (1) and (2).

In the third embodiment, it is desired to satisfy the above-mentioned Conditional Expression (2-1).

Alcohol may be used as the medium on the sample 108 side. It is therefore preferred to set the lower limit value in Conditional Expression (2-1) to be $1.5 \times 10^6$ (kg/(m²s)), which is the acoustic impedance value of water.

It is desired that the medium of the main acoustic lens 105 be glass. Glass has high transmittance to the excitation light L and is advantageous for the correction of the photoacoustic waves (ultrasonic waves) U, and is therefore suited for the main acoustic lens 105. Glass has high acoustic impedance, but the use of the above-mentioned correction acoustic lens 106 can reduce the reflection of ultrasonic waves (photoacoustic waves) traveling from the sample 108 at the interface.

It is desired that the correction acoustic lens 106 satisfy the above-mentioned Conditional Expression (3).

It is desired that the correction acoustic lens 106 satisfy the above-mentioned Conditional Expression (4).

It is desired that the correction acoustic lens 106 satisfy the above-mentioned Conditional Expression (5).

It is desired that the difference between the thickness d of the correction acoustic lens 106 on the optical axis AX and the thickness dp of the correction acoustic lens 106 at a peripheral portion be larger than a half of the wavelength $\lambda$ of the photoacoustic wave U in the air.

It is desired that a surface of the correction acoustic lens 106 on the sample 108 side be a concave surface or a flat surface.

It is desired that the correction acoustic lens 106 satisfy at least one of the above-mentioned Conditional Expression (6-1) or Conditional Expression (6-2).

In the third embodiment, the correction acoustic lens 106 is formed of a material obtained by solidifying water with agarose.

Fourth Embodiment

Figure 4:
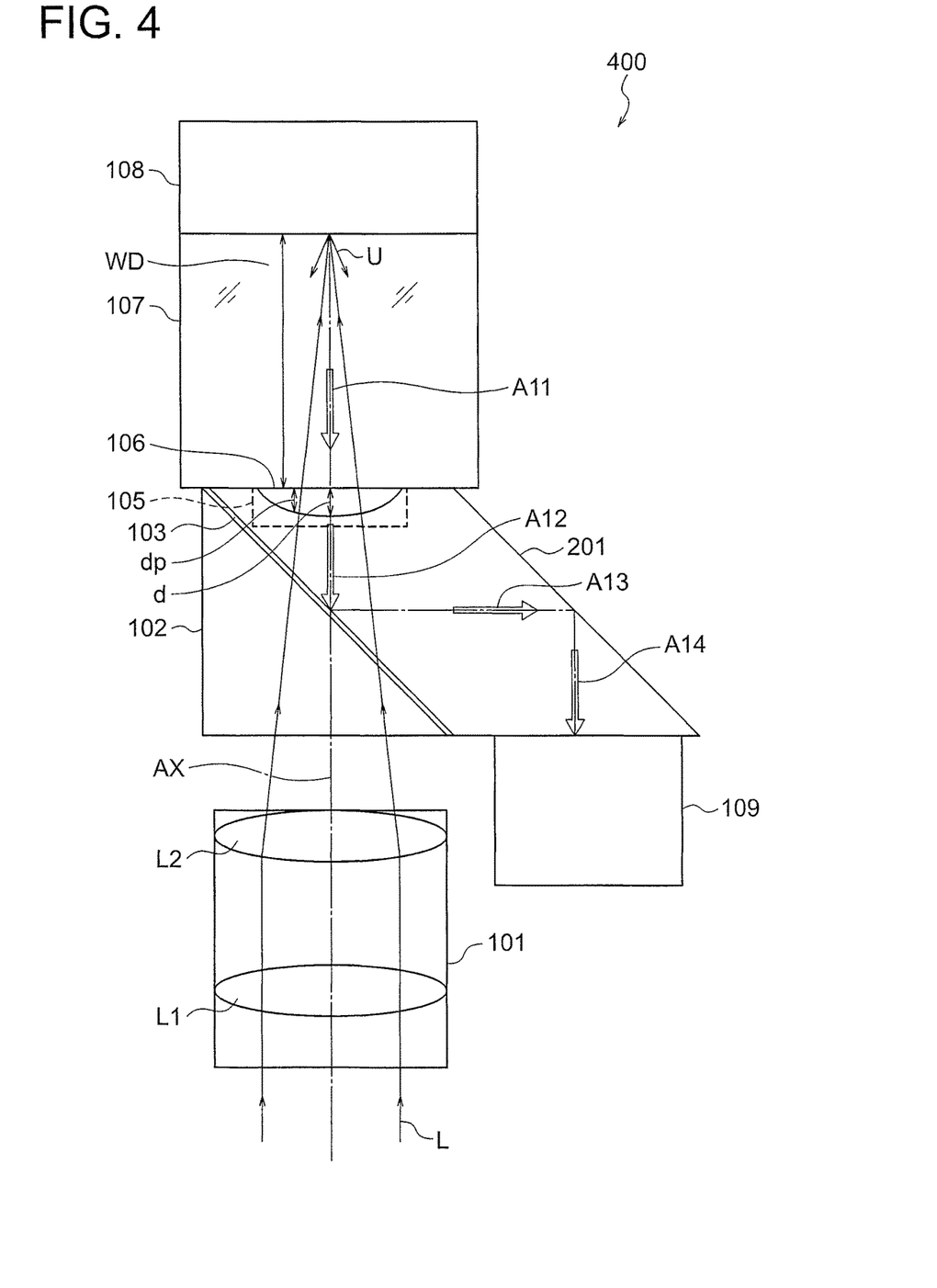
FIG. 4 is a diagram illustrating a configuration of a photoacoustic microscope objective lens unit according to a fourth embodiment of the present invention.

FIG. 4 illustrates a schematic configuration of a photoacoustic microscope objective lens unit 400 according to a fourth embodiment of the present invention. The same parts as in the third embodiment are denoted by the same reference symbols to omit overlapping descriptions. The photoacoustic microscope objective lens unit in the fourth embodiment is suitable for inverted illumination.

Excitation light (pulse light) L from a laser pulse light source (not shown) passes through the objective lens 101, the triangular prism 102, the photoacoustic wave reflective member 103, the rhomboid prism (rhomboidal prism) 201, the main acoustic lens 105 (indicated by dotted line in FIG. 4), and the correction acoustic lens 106 to irradiate the sample 108. The applied excitation light L is focused on the surface or in the inside of the sample 108. The main acoustic lens 105 and the correction acoustic lens 106 are formed in the rhomboid prism 201.

A photoacoustic wave transmission medium 107 through which photoacoustic waves U easily propagate, such as water, is filled between the rhomboid prism 201 and the sample 108.

When an object to be observed that absorbs the excitation light L is present at an irradiation region of the excitation light L including the focus position of the objective lens 101, the excitation light L applied to the sample 108 is absorbed by the object to be observed. In response thereto, photoacoustic waves U as elastic waves are generated from the sample 108. The generated photoacoustic waves U pass through the correction acoustic lens 106, the main acoustic lens 105, and the rhomboid prism 201 to be detected by the ultrasound transducer 109. The triangular prism 102, the photoacoustic wave reflective member 103, and the rhomboid prism 201 form a photoacoustic wave separation member. The photoacoustic wave separation member transmits the excitation light L traveling from the objective lens 101 and reflects the photoacoustic waves U generated from the sample 108.

In addition, the triangular prism 102, the photoacoustic wave reflective member 103, the rhomboid prism 201, the main acoustic lens 105, and the correction acoustic lens 106 form a photoacoustic wave guide system.

Photoacoustic waves U generated from the sample 108 are focused by the correction acoustic lens 106 and the main acoustic lens 105 to enter the rhomboid prism 201 as focused waves. The focused waves are reflected by an inclined plane of the rhomboid prism 201 with acoustic impedance of the photoacoustic wave reflective member 103. The photoacoustic wave reflective member 103 is preferably designed such that the refractive index for the excitation light L substantially matches with refractive indices of the triangular prism 102 and the rhomboid prism 201 and the thickness is as small as possible. This configuration can prevent unnecessary refraction and light absorption by the photoacoustic wave reflective member 103, thereby improving use efficiency of the excitation light L.

The photoacoustic waves U reflected by the inclined plane of the rhomboid prism 201 in the direction of the arrow A12 are reflected by another inclined plane of the rhomboid prism 201 in the direction of the arrow A13 and output from the rhomboid prism 201. The output photoacoustic waves U are detected by the ultrasound transducer 109. At least the triangular prism 102, the photoacoustic wave reflective member 103, and the rhomboid prism 201 forma photoacoustic wave separation member. The photoacoustic wave separation member transmits the excitation light L traveling from the objective lens 101 and reflects the photoacoustic waves U generated from the sample 108.

In addition, the triangular prism 102, the photoacoustic wave reflective member 103, the rhomboid prism 201, the main acoustic lens 105, and the correction acoustic lens 106 form a photoacoustic wave guide system.

In the fourth embodiment, the rhomboid prism 201 includes the main acoustic lens 105 and the correction acoustic lens 106.

As described above, in the photoacoustic microscope objective lens unit 100 according to the fourth embodiment, the acoustic lens is formed by cementing a main acoustic lens 105 disposed on the photoacoustic wave reflective member 103 side and a correction acoustic lens 106 disposed on the sample 108 to suppress the reflection of the photoacoustic waves U.

The acoustic lens is disposed between the photoacoustic wave separation member and the sample 108, and has a focus position that substantially matches with the focus position of the objective lens 101. For example, the acoustic lens converts the wavefront of the photoacoustic wave U into a flat wavefront.

It is desired that the main acoustic lens 105 and the correction acoustic lens 106 satisfy the above-mentioned Conditional Expressions (1) and (2).

In the fourth embodiment, it is desired to satisfy the above-mentioned Conditional Expression (2-1).

In particular, when the sample 108 is a biological sample, the medium on the sample 108 is generally water. Alcohol may be used as the medium on the sample side. It is therefore preferred to set the lower limit value in Conditional Expression (2-1) to be $1.5 \times 10^6$ (kg/(m²s)), which is the acoustic impedance value of water.

It is desired that the medium of the main acoustic lens 105 be glass. Glass has high transmittance to the excitation light L and is advantageous for the correction of the photoacoustic waves (ultrasonic waves) U, and is therefore suited for the main acoustic lens 105. Glass has high acoustic impedance, but the use of the above-mentioned correction acoustic lens 106 can reduce the reflection of ultrasonic waves (photoacoustic waves) traveling from the sample 108 at the interface.

It is desired that the correction acoustic lens 106 satisfy the above-mentioned Conditional Expression (3).

It is desired that the correction acoustic lens 106 satisfy the above-mentioned Conditional Expression (4).

It is desired that the correction acoustic lens 106 satisfy the above-mentioned Conditional Expression (5).

It is desired that the difference between the thickness d of the correction acoustic lens 106 on the optical axis AX and the thickness dp of the correction acoustic lens 106 at a peripheral portion be larger than a half of the wavelength λ of the photoacoustic wave U in the air.

It is desired that a surface of the correction acoustic lens 106 on the sample 108 side be a concave surface or a flat surface.

It is desired that the correction acoustic lens 106 satisfy at least one of the above-mentioned Conditional Expression (6-1) or Conditional Expression (6-2).

In the fourth embodiment, the correction acoustic lens 106 is formed of a material obtained by solidifying water with agarose.

Fifth Embodiment

Figure 5:
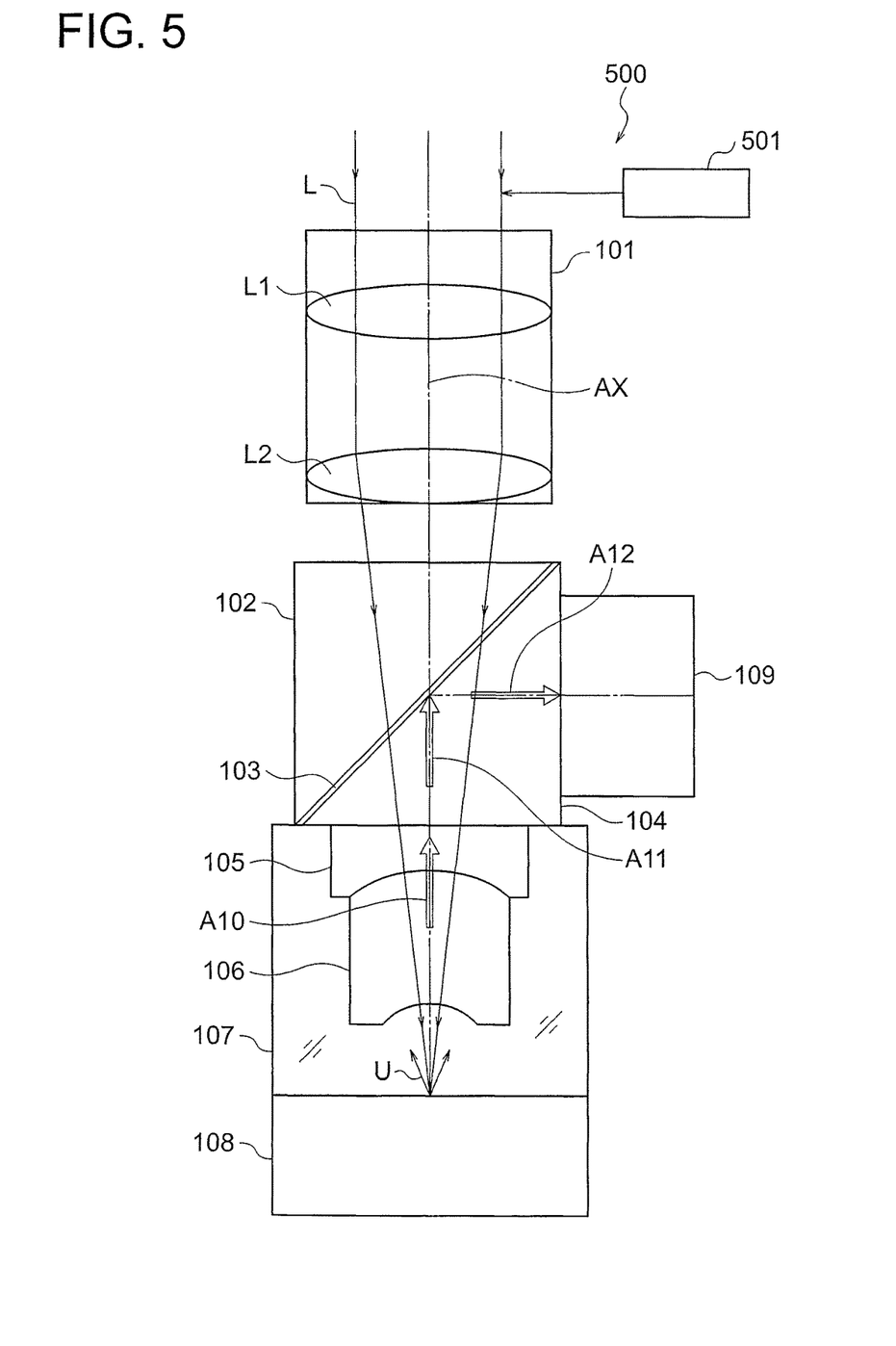
FIG. 5 is a diagram illustrating a configuration of a photoacoustic microscope objective lens unit according to a fifth embodiment of the present invention.

FIG. 5 illustrates a schematic configuration of a photoacoustic microscope 500 including the photoacoustic microscope objective lens unit according to the first embodiment. The same parts as in the above-mentioned first embodiment are denoted by the same reference symbols to omit overlapping descriptions.

The photoacoustic microscope 500 according to the fifth embodiment includes, for example, the photoacoustic microscope objective lens unit 100, and a scanning unit 501 which scan the sample 108 with excitation light L while moving an irradiation position of the excitation light L.

In this manner, a one-dimensional, two-dimensional, or three-dimensional photoacoustic image signal can be obtained depending on the manner of scanning.

The scanning unit 501 is which scan an irradiation position of the excitation light L on the sample 108. A publicly known configuration, such as a galvanometer mirror, is used to move the excitation light L with respect to the sample 108, move a sample stage (not shown) on which the sample 108 is placed, or move both the excitation light L and the sample stage. The movement direction may be two-dimensional directions within a plane orthogonal to the direction of the optical axis AX of the objective lens 101, a one-dimensional direction as only the direction of the optical axis AX of the objective lens 101, or three-dimensional directions including the movement directions of the excitation light L and the sample stage.

For acquiring a tomographic image of the sample 108, the scanning unit 501 is used to scan the sample 108 with excitation light L in a two-dimensional manner within a plane orthogonal to the optical axis AX of the objective lens 101. A processor (not shown) is used to process an output signal from the ultrasound transducer 109 in synchronization with an irradiation timing of the excitation light L, thereby obtaining a tomographic image.

For detecting a distribution of an object to be observed in a depth direction of the sample 108, the scanning unit 501 is used to scan the sample 108 with excitation light L in the direction of the optical axis AX of the objective lens 101. A processor (not shown) is used to process an output signal from the ultrasound transducer 109 in synchronization with an irradiation timing of the excitation light L, thereby obtaining an image of the distribution of the object to be observed in the depth direction of the sample 108.

The photoacoustic microscope objective lens units according to the second embodiment to the fourth embodiment can be used to configure a photoacoustic microscope.

Next, conditional expression correspondence values in each embodiment are described below.

"E+n" (n is an integer) represents "$10^n$".

Further, ex1, ex2, ex3 and ex4 denote "First Embodiment", "Second Embodiment", "Third Embodiment" and "Fourth Embodiment" respectively,

| Impedance of acoustic lens | | | | |
|---|---|---|---|---|
| | ex1 | ex2 | ex3 | ex4 |
| Z1 (kg/m$^2$s) | 1.4346E+07 | 1.7687E+07 | 1.7687E+07 | 1.7687E+07 |

| Impedance of correction acoustic lens | | | | |
|---|---|---|---|---|
| | ex1 | ex2 | ex3 | ex4 |
| Z0 (kg/m$^2$s) | 5.1508E+06 | 4.9000E+06 | 4.6389E+06 | 4.6389E+06 |

| Impedance of water | | | | |
|---|---|---|---|---|
| | ex1 | ex2 | ex3 | ex4 |
| Z2 (kg/m$^2$s) | 1.5000E+06 | 1.5000E+06 | 1.5000E+06 | 1.5000E+06 |

| Refractive index of acoustic lens | | | | |
|---|---|---|---|---|
| | ex1 | ex2 | ex3 | ex4 |
| n1 | 1.794818 | 1.5195 | 1.5195 | 1.5195 |

| Refractive index of water | | | | |
|---|---|---|---|---|
| | ex1 | ex2 | ex3 | ex4 |
| n2 | 1.3300 | 1.3300 | 1.3300 | 1.3300 |

| Sound speed in acoustic lens | | | | |
|---|---|---|---|---|
| | ex1 | ex2 | ex3 | ex4 |
| V1 (m/s) | 5715.71 | 4405.60 | 4405.60 | 4405.60 |

| Sound speed in correction acoustic lens | | | | |
|---|---|---|---|---|
| | ex1 | ex2 | ex3 | ex4 |
| V0 (m/s) | 3000.00 | 2650 | 2500.00 | 2500.00 |

| Sound speed in water | | | | |
|---|---|---|---|---|
| | ex1 | ex2 | ex3 | ex4 |
| V2 (m/s) | 1500.00 | 1500.00 | 1500.00 | 1500.00 |

| Thickness of correction acoustic lens | | | | |
|---|---|---|---|---|
| | ex1 | ex2 | ex3 | ex4 |
| d (mm) | 2 | 1.5 | 1 | 0.5 |

| Transmittance of correction acoustic lens | | | | |
|---|---|---|---|---|
| | ex1 | ex2 | ex3 | ex4 |
| T0 | 0.92 | 0.9 | 0.95 | 0.95 |

| Refractive index of correction acoustic lens | | | | |
|---|---|---|---|---|
| | ex1 | ex2 | ex3 | ex4 |
| n0 | 1.35 | 1.55 | 1.33 | 1.33 |

| Scattering coefficient of correction acoustic lens | | | | |
|---|---|---|---|---|
| | ex1 | ex2 | ex3 | ex4 |
| s (1/mm) | 0.05 | 0.1 | 0.1 | 0.1 |

| Absorption coefficient of correction acoustic lens | | | | |
|---|---|---|---|---|
| | ex1 | ex2 | ex3 | ex4 |
| $\alpha$ (1/mm) | 0.05 | 0.1 | 0.1 | 0.1 |

| Sound speed to be detected | | | | |
|---|---|---|---|---|
| | ex1 | ex2 | ex3 | ex4 |
| MHz | 20 | 30 | 20 | 10 |

| Wavelength | | | | |
|---|---|---|---|---|
| | ex1 | ex2 | ex3 | ex4 |
| mm | 0.285785421 | 0.146853225 | 0.220279837 | 0.440559675 |

| Conditional Expression (1) T0 | | | | |
|---|---|---|---|---|
| | ex1 | ex2 | ex3 | ex4 |
| | 0.92 | 0.9 | 0.95 | 0.95 |

| Conditional Expression (2) $Z2 < Z0 < Z1$ | | | | |
|---|---|---|---|---|
| | ex1 | ex2 | ex3 | ex4 |
| Z2 | 1.50E+06 | 1.50E+06 | 1.50E+06 | 1.50E+06 |
| Z0 | 5.15E+06 | 4.90E+06 | 4.64E+06 | 4.64E+06 |
| Z1 | 1.43E+07 | 1.77E+07 | 1.77E+07 | 1.77E+07 |

| Conditional Expression (3) $s \times d < (Z2 - Z1)^2/(Z2 + Z1)^2$ | | | | |
|---|---|---|---|---|
| | ex1 | ex2 | ex3 | ex4 |
| s × d | 0.1 | 0.15 | 0.1 | 0.05 |
| $(Z2 - Z1)^2/(Z2 + Z1)^2$ | | | | |
| | ex1 | ex2 | ex3 | ex4 |
| | 0.657206746 | 0.711739324 | 0.711739324 | 0.711739324 |

| Conditional Expression (4) $\alpha \times d < (Z2 - Z1)^2/(Z2 + Z1)^2$ | | | | |
|---|---|---|---|---|
| | ex1 | ex2 | ex3 | ex4 |
| α × d | 0.1 | 0.15 | 0.1 | 0.05 |
| $(Z2 - Z1)^2/(Z2 + Z1)^2$ | | | | |
| | ex1 | ex2 | ex3 | ex4 |
| | 0.657206746 | 0.711739324 | 0.711739324 | 0.711739324 |

| Conditional Expression (5) $d/\lambda$ | | | | |
|---|---|---|---|---|
| | ex1 | ex2 | ex3 | ex4 |
| λ | 0.28579 | 0.14685 | 0.22028 | 0.44056 |
| d | 2 | 1.5 | 1.0 | 0.5 |

| Conditional Expression (6) $|n0 - n2| < 0.1$ or $|n0 - n1| < 0.1$ | | | | |
|---|---|---|---|---|
| | ex1 | ex2 | ex3 | ex4 |
| n0 − n2 | 0.0200 | 0.2200 | 0.0000 | 0.0000 |
| n0 − n1 | 0.4448 | −0.0305 | 0.1895 | 0.1895 |

As described above, the present invention is effective to a photoacoustic microscope objective lens unit capable of efficiently irradiating a sample with excitation light and detecting a photoacoustic wave from the sample without any loss, and a photoacoustic microscope including the photoacoustic microscope objective lens unit.

The present invention exhibits effects that a photoacoustic microscope objective lens unit capable of efficiently irradiating a sample with excitation light and detecting a photoacoustic wave from the sample without any loss, and a photoacoustic microscope including the photoacoustic microscope objective lens unit can be provided.

What is claimed is:

1. A photoacoustic microscope objective lens unit, comprising:
    an objective lens which irradiates a sample with excitation light having an absorption wavelength band of an object to be observed;

a photoacoustic wave detection unit which detects a photoacoustic wave generated from the sample through irradiation of the excitation light; and a photoacoustic wave guide system which guides the photoacoustic wave to the photoacoustic wave detection unit, wherein the photoacoustic wave guide system comprises:

a photoacoustic wave separation member which transmits the excitation light traveling from the objective lens and reflects the photoacoustic wave generated from the sample; and an acoustic lens that is disposed between the photoacoustic wave separation member and the sample and has a focus position that substantially matches with a focus position of the objective lens, the acoustic lens is formed by cementing a main acoustic lens to a correction acoustic lens, the main acoustic lens being disposed between the photoacoustic wave separation member and the correction acoustic lens and the correction acoustic lens being disposed between the sample and the main acoustic lens to suppress reflection of the photoacoustic wave, and the main acoustic lens and the correction acoustic lens satisfy the following Conditional Expressions (1), (2) and (3):

$$0.8 < T0 \leq 1.0 \quad (1)$$

$$Z2 < Z0 < Z1 \quad (2)$$

$$s \times d < (Z2-Z1)^2/(Z2+Z1)^2 \quad (3)$$

where

T0 is a transmittance of the correction acoustic lens with respect to the excitation light on an optical axis, Z0 is acoustic impedance of a medium of the correction acoustic lens, Z1 is acoustic impedance of a medium of the main acoustic lens, Z2 is acoustic impedance of a medium that is brought into contact with the correction acoustic lens on the sample side during detection of the photoacoustic wave;

s is a scattering coefficient of the medium of the correction acoustic lens with respect to the excitation light, and d is a thickness of the correction acoustic lens on an optical axis.

2. The photoacoustic microscope objective lens unit according to claim 1, wherein the following Conditional Expression (2-1) is satisfied:

$$1.5 \times 10^6 (kg/(m^2 s)) < Z0 < Z1 \quad (2-1)$$

where

Z0 is the acoustic impedance of the medium of the correction acoustic lens, and

Z1 is the acoustic impedance of the medium of the main acoustic lens.

3. The photoacoustic microscope objective lens unit according to claim 1, wherein the medium of the main acoustic lens comprises glass.

4. The photoacoustic microscope objective lens unit according to claim 1, wherein the correction acoustic lens satisfies the following Conditional Expression (4):

$$\alpha \times d < (Z2-Z1)^2/(Z2+Z1)^2 \quad (4)$$

where a is an absorption coefficient of the medium of the correction acoustic lens with respect to the excitation light, d is the thickness of the correction acoustic lens on an optical axis, and Z1 is the acoustic impedance of the medium of the main acoustic lens, and Z2 is the acoustic impedance of the medium that is brought into contact with the correction acoustic lens on the sample side during detection of the photoacoustic wave.

5. The photoacoustic microscope objective lens unit according to claim 1, wherein the correction acoustic Ions satisfies the following Conditional Expression (5):

$$1.0 < d/\lambda \quad (5)$$

where d is the thickness of the correction acoustic lens on the optical axis, and X is the wavelength of the photoacoustic wave in air.

6. The photoacoustic microscope objective lens unit according to claim 1, wherein a difference between the thickness of the correction acoustic lens on the optical axis and the thickness of the correction acoustic lens at a peripheral part is equal to or larger than a half of a wavelength X of the photoacoustic wave in air.

7. The photoacoustic microscope objective lens unit according to claim 1, wherein a surface of the correction acoustic lens on the sample side is a concave surface or a flat surface.

8. The photoacoustic microscope objective lens unit according to claim 1, wherein the correction acoustic lens satisfies at least one of the following Conditional Expression (6-1) and Conditional Expression (6-2):

$$|n0-n2|<0.1 \quad (6-1)$$

$$|n0-n1|<0.1 \quad (6-2)$$

where n0 is a refractive index of the medium of the correction acoustic lens with respect to the excitation light, n1 is a refractive index of the medium of the main acoustic lens with respect to the excitation light, and n2 is a refractive index of a medium that is brought into contact with the correction acoustic lens on the sample side with respect to the excitation light during detection of the photoacoustic wave.

9. The photoacoustic microscope objective lens unit according to claim 1, wherein the correction acoustic lens is formed of a material obtained by solidifying water with a coagulant into a gel.

10. A photoacoustic microscope, comprising:

the photoacoustic microscope objective lens unit according to claim 1; and a scanning unit which scans the sample with the excitation light while moving an irradiation position of the excitation light.

* * * * *